(12) United States Patent
Tuinstra et al.

(10) Patent No.: US 9,512,437 B2
(45) Date of Patent: Dec. 6, 2016

(54) GENETIC MUTATIONS THAT DISRUPT DHURRIN PRODUCTION IN SORGHUM

(71) Applicant: PURDUE RESEARCH FOUNDATION, West Lafayette, IN (US)

(72) Inventors: Mitchell R. Tuinstra, West Lafayette, IN (US); Kartikeya Krothapalli, West Lafayette, IN (US); Brian Dilkes, West Lafayette, IN (US); Elizabeth Buescher, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 0 days.

(21) Appl. No.: 14/423,927

(22) PCT Filed: Aug. 16, 2013

(86) PCT No.: PCT/US2013/055256
§ 371 (c)(1),
(2) Date: Feb. 25, 2015

(87) PCT Pub. No.: WO2014/035685
PCT Pub. Date: Mar. 6, 2014

(65) Prior Publication Data
US 2015/0218576 A1 Aug. 6, 2015

Related U.S. Application Data

(60) Provisional application No. 61/779,634, filed on Mar. 13, 2013, provisional application No. 61/693,974, filed on Aug. 28, 2012.

(51) Int. Cl.
*C12N 15/82* (2006.01)
*A01H 5/10* (2006.01)
*A01H 1/06* (2006.01)

(52) U.S. Cl.
CPC ............. *C12N 15/8245* (2013.01); *A01H 1/06* (2013.01); *A01H 5/10* (2013.01)

(58) Field of Classification Search
None
See application file for complete search history.

(56) References Cited

FOREIGN PATENT DOCUMENTS

| EP | 1510586 | 3/2005 |
|----|---------|--------|
| WO | WO2012-126059 | 9/2012 |

OTHER PUBLICATIONS

Blomstedt et al 2012 Plant Biotechnology Journal 10:54-66.*
Akazawa, T., P. Miljanich, et al. (1960). "Studies on the cyanogenic glucoside of Sorghum vulgare." Plant Physiol 35: 535-538.
Bak, S., S. Paquette, et al. (2006). "Cyanogenic glucosides: a case study for evolution and application of cytochromes P450." Phytochem Rev 5: 309-329.
Banea-Mayambu, J. P., T. Tylleskar, et al. (1997). "Geographical and seasonal association between linamarin and cyanide exposure from cassava and the upper motor neurone disease Konzo in former Zaire" Trop. Med. Int. Health 2: 1143-1151.
Banea-Mayambu, J. P., T. Tylleskar, et al. (2000). "Dietary cyanide from insufficiently processed cassava and growth retardation in children in the Democratic Republic of Congo (formerly Zaire)." Ann. Trop. Paediatr 20: 34-40.
Blomstedt, C.K., et al. (2012). "A combined biochemical screen and TILLING approach identifies mutations in Sorghum bicolor L. Moench resulting in acyanogenic forage production." Plant Biotechnology Journal 10: 54-66.
Boyd, F. T., O. S. Aamodt, et al. (1938). "Sudan grass management for control of cyanide poisoning." J Am Soc Agron 30: 569-582.
Brattsten, L. B., J. H. Samuelian, et al. (1983). "Cyanide as a feeding stimulant for the southern armyworm, Spodoptera eridania." Ecol. Entomology 8: 125-132.
Busk, P.K. et al. (2002) "Dhurrin synthesis in sorghum is regulated at the transcriptional level and induced by nitrogen fertilization in older plants." Plant Physiology 129:1222-1231.
Casa, A. M. (2008). "Community resources and strategies for association mapping in sorghum." Crop Science 48: 30-40.
Conn, E. E. (1994). "Cyanogenesis—a personal perspective." Acta Hort. 375: 31-43.
De Nicola, G.R., Leoni, O., Malaguti, L., Bernardi, R., Lazzeri, L. (2011) A simple analytical method for dhurrin content evaluation in cyanogenic plants for their utilization in fodder and, biofumigation J. Agric. Food Chem., 59: 8065-8069.
Feigl, F. and V. Anger (1966). "Replacement of benzidine by copper ethylacetoacetate and tetra base as spot-test reagent for hydrogen cyanide and cyanogen." Analyst (Lond.) 91: 282-284.
Goodstein, D. M. et al., Phytozome: a comparative platform for green plant genomics, Nucleic Acids Res. 2012 40 (D1): D1178-D1186.
Gorz, H. J., W. L. Haag, et al. (1977). "Assay of p-hydroxybenzaldehyde as a measure of hydrocyanic acid potential in sorghums." Crop Science 17: 578-582.
Halkier, B. A. and B. L. Moller (1989). "Biosynthesis of the cyanogenic glucoside dhurrin in seedlings of Sorghum-bicolor (L.) Moench and partial-purification of the enzyme-system involved." Plant Physiol 90: 1552-1559.

(Continued)

*Primary Examiner* — Brent Page
(74) *Attorney, Agent, or Firm* — Marianne Fuierer; Tristan Anne Fuierer; Moore & Van Allen, PLLC

(57) ABSTRACT

Embodiments of the present invention relate generally to new forage crops and methods of creating new forage crops. For example, chemical mutagenesis is used to create mutant crops having desirable forage characteristics. In some embodiments, a mutant *sorghum* plant is produced by inducing mutagenesis; producing a population of mutant *sorghum* plants using the treated reproductive portion; assaying the population of mutant *sorghum* for a C493Y mutation in CYP79A1; and growing the mutant *sorghum* plant, wherein the mutant *sorghum* plant exhibits altered dhurrin content or catabolism as compared to a control *sorghum* plant.

18 Claims, 5 Drawing Sheets

(56) References Cited

OTHER PUBLICATIONS

Jaroszewski, J. W., E. S. Olafsdottir, et al. (2002). "Cyanohydrin glycosides of Passiflora: distribution pattern, a saturated cyclopentane derivative from P. guatemalensis, and formation of pseudocyanogenic [alpha]-hydroxyamides as isolation artefacts." Phytochemistry 59(5): 501-511.

Lin, Y. R., K. F. Schertz, et al. (1995). "Comparative analysis of QTLs affecting plant height and maturity across the Poaceae, in reference to an interspecific sorghum population." Genetics 141: 391-411.

Oluwole, O. S. A., A. O. Onabolu, et al. (2000). "Persistence of tropical ataxic neuropathy in a Nigerian community." J Neurol Neurosurg Psychiatr 69: 96-101.

Osbourn, A. E. (1996). "Preformed antimicrobial compounds and plant defense against fungal attack." Plant Cell 8: 1821-1831.

Paterson A. H., et al. (2009). "The Sorghum bicolor genome and the diversification of grasses." Nature 457, 551-556.

Prasad, S., et al. 2011. "Determination and detoxification of cyanide content in sorghum for ethanol production using *Saccharomyces cerevisiae* strain." Journal of Metabolomics and Systems Biology. 2: 10-14.

Robinson, M. E. (1930). "Cyanogenesis in plants." Biol. Rev. 5: 126-142.

Stephens, J. C., F. R. Miller, et al. (1967). "Conversion of alien sorghums to early combine genotypes." Crop Science 7: 396.

Thorsoe, K.S. et al. (2005) "Determination of catalytic key amino acids and UDP sugar donor specificity of the cyanohydrin glycosyltransferase UGT85B1 from Sorghum bicolor. Molecular modeling substantiated by site-specific mutagenesis and biochemical analyses." Plant Physiology 139:664-673.

VanEtten, H. D., J. W. Mansfield, et al. (1994). "2 classes of plant antibiotics—phytoalexins versus phytoanticipins." Plant Cell 6: 1191-1192.

Vetter, J. (2000). "Plant cyanogenic glycosides." Toxicon 38: 11-36.

Webber, J. J., C. R. Roycroft, et al. (1985). "Cyanide poisoning of goats from sugar gums (*Eucalyptus cladocalyx*)." Aust. Vet. J.: 62:28.

Zagrobelny, M., S. Bak, et al. (2008). "Cyanogenesis in plants and arthropods." Phytochemistry 69: 1457-1468.

\* cited by examiner

SEQ ID NO: 1

```
1    matmeveaaa atvlaaplls ssailklllf vvtlsylara lrrprksttk cssttcaspp
61   agvgnpplpp gpvpwpvvgn lpemllnkpa frwihqmmre mgtdiacvkl ggvhvvsitc
121  peiarevlrk qdanfisrpl tfasetfsgg yrnavlspyg dqwkkmrrvl tseiicpsrh
181  awlhdkrtde adnltryvyn latkaatgdv avdvrhvarh ycgnvirrlm fnrryfgepq
241  adggpgpmev lhmdavftsl gllyafcvsd ylpwlrgldl dghekivkea nvavnrlhdt
301  viddrwrqwk sgerqemedf ldvlitlkda qgnplltiee vkaqsqditf aavdnpsnav
361  ewalaemvnn pevmakamee ldrvvgrerl vqesdipkln yvkacireaf rlhpvapfnv
421  phvaladtti agyrvpkgsh vilsrtglgr nprvwdeplr fypdrhlata asdvaltend
481  lrfisfstgr rgciaaslgt amsvmlfgrl lqgftwskpa gveavdlses ksdtfmatpl
541  vlhaeprlpa hlypsisi
```

SEQ ID NO: 2

```
1    matmeveaaa atvlaaplls ssailklllf vvtlsylara lrrprksttk cssttcaspp
61   agvgnpplpp gpvpwpvvgn lpemllnkpa frwihqmmre mgtdiacvkl ggvhvvsitc
121  peiarevlrk qdanfisrpl tfasetfsgg yrnavlspyg dqwkkmrrvl tseiicpsrh
181  awlhdkrtde adnltryvyn latkaatgdv avdvrhvarh ycgnvirrlm fnrryfgepq
241  adggpgpmev lhmdavftsl gllyafcvsd ylpwlrgldl dghekivkea nvavnrlhdt
301  viddrwrqwk sgerqemedf ldvlitlkda qgnplltiee vkaqsqditf aavdnpsnav
361  ewalaemvnn pevmakamee ldrvvgrerl vqesdipkln yvkacireaf rlhpvapfnv
421  phvaladtti agyrvpkgsh vilsrtglgr nprvwdeplr fypdrhlata asdvaltend
481  lrfisfstgr rgyiaaslgt amsvmlfgrl lqgftwskpa gveavdlses ksdtfmatpl
541  vlhaeprlpa hlypsisi
```

FIG. 5

GENETIC MUTATIONS THAT DISRUPT DHURRIN PRODUCTION IN SORGHUM

CROSS-REFERENCE TO RELATED APPLICATIONS

This application is filed under the provisions of 35 U.S.C. §371 and claims the priority of International Patent Application No. PCT/US2013/55256 filed on 16 Aug. 2013 entitled "GENETIC MUTATIONS THAT DISRUPT DHURRIN PRODUCTION IN SORGHUM" in the name of Mitchell R. TUINSTRA et al., which claims priority to U.S. Provisional Patent Application No. 61/693,974 filed on 28 Aug. 2012, both of which are hereby incorporated by reference herein in their entirety.

STATEMENT AS TO U.S. GOVERNMENT INTERESTS IN INVENTIONS MADE UNDER FEDERALLY SPONSORED RESEARCH AND DEVELOPMENT

This invention was made with government support under EPP-A-06-0016-00 awarded by the United States Agency for International Development. The government has certain rights in the invention.

BACKGROUND

Sorghum (*Sorghum biocolor* (L.) Moench) is recognized as a low-input forage and bioenergy crop that is highly resilient to the effects of climate change. The crop generally requires about half the water to grow compared to corn and exhibits excellent adaptation to low-input production systems. Given these characteristics, it is one of the most highly-touted of the new bioenergy crops identified for use in future biomass production systems.

Sorghum produces a large number of secondary metabolites including the cyanogenic glucoside dhurrin. Cyanogenic glucosides belong to a class of plant-produced antibiotics called phytoanticipins (Vanetten et al., 1994; Osbourn et al., 1996). More than 2,650 plant species are cyanogenic and able to release HCN upon tissue disruption (Conn, 1981; Siegler and Brinker, 1993) including pteridophytes, gymnosperms and angiosperms. Phylogenetic analyses suggest the evolution of cyanogenesis occurred before the bifurcation of pteridophytes and gymnosperms. Cyanogenic glucosides are particularly important in crop plants used for animal and human nutrition such as *sorghum*, barley [*Hordium vulgare* L.], and cassava [*Manihot esculenta* Crantz].

Biochemical studies have shown that plant cyanogenic glucosides are derived from six different amino acids: the aliphatic protein amino acids valine, isoleucine and leucine; the aromatic amino acids phenylalanine and tyrosine; and the aliphatic nonproteinogenic amino acid cyclopentenyl glycine (Jones, 2000; Jaroszewski et al., 2002). Fern and gymnosperm species generally produce cyanogenic glucosides from the aromatic amino acids, whereas angiosperms produce cyanogenic glucosides from aliphatic and aromatic amino acids (Bak et al., 2006). Arthropods including millipedes (Diploda), centipedes (Chilopoda), beetles (Coleoptera), and true bugs (Heteroptera) also produce cyanogenic glucosides that are synthesized from aromatic amino acids or in the case of lepidopterans from aliphatic amino acids (Bak et al., 2006; Zagrobelny et al., 2008).

When plant tissues are disrupted through chewing or tissue maceration, the cyanogenic glucosides in the vacuoles are brought into contact with β-glucosidases and α-hydroxynitrile lyases that hydrolyze the cyanogenic glucosides and produce HCN (Vetter et al., 2000). This HCN renders the consumption of plant materials containing cyanogenic glucosides toxic to humans and most animals (Oluwole et al., 2000). The affinity of cyanide for the terminal cytochrome oxidase in the mitochondrial respiratory pathway is the main cause of toxicity (Brattsten et al., 1983). A lethal dose of cyanide for vertebrate animals is in the range of 35-150 μmol kg-1, but higher amounts can be tolerated if consumed over a longer period (Davis and Nahrstedt, 1985). Studies in horses showed that *sorghum*-based diets consumed over a 2-month period resulted in incoordination of the hind legs, urinary incontinence, and haematuria. These symptoms were followed by increased nasal discharge, increased body temperature, and depression of appetite (Varshney et al., 1996).

Given the toxicity of HCN, cyanogenic glucosides are assumed to play a role in plant defense against animal and insect herbivores. The effects of cyanogenic plants in human and animal health is well documented (Banea-Mayambu et al., 1997, 2000; Robinson, 1930; Boyd, 1938; Webber et al., 1985; Hopkins et al., 1995). In the case of *sorghum* forage, cyanide poisoning resulting in cattle death was first reported in Australia more than a hundred years ago (Anon, 1897).

Sorghum was used as the model to dissect the cyanogenic glucoside biosynthetic pathway in plants. All of the structural genes in this pathway have been cloned (Jones et al., 2000) (FIG. 1). The *S. bicolor* genome was sequenced and is available from the Phytozome project, which is a joint project of the Department of Energy's Joint Genome Institute and the Center for Integrative Genomics, at http://www.phytozome.net/*sorghum*. The sequenced genome consists of 697,578,683 base pairs arranged in 2n=20 chromosomes. It has 34,496 loci containing protein-coding transcripts and 36,338 protein-coding transcripts. The *S. bicolor* genome was published in Paterson et al. 2009 and will be referred to herein by its identifier Tx623.

Dhurrin is a cyanogenic glucoside of *sorghum* and dhurrin accumulation in plant tissues negatively impacts forage and feedstock quality. *Sorghum* breeders are working to modify dhurrin content to improve forage and biomass quality but are constrained by a lack of natural genetic variation for this trait in the elite *sorghum* gene pool. Mutation breeding is being used to induce mutations in the dhurrin biosynthesis pathways. One mutant was recently identified in Australia that produced no dhurrin in any tissue but exhibited "slightly slower growth at early seedling stage." (Blomstedt, 2012). Different mutations or alleles that similarly disrupt dhurrin biosynthesis but without impacts on growth may be better suited to commercial product development.

Dhurrin content is highest in young seedlings and can represent as much as 6 to 10% of the dry weight of plants (Akazawa et al., 1960; Conn, 1994). Accumulations as high as 30% dry weight have been reported in some parts of *sorghum* seedlings (Halkier et al., 1989). However, little is known about the downstream processing and utilization of cyanogenic glucosides in *sorghum* or any other plant species.

Thus, there is a need for a low-dhurrin or dhurrin-free *sorghum* plant that has a standard growth rate compared to existing commercial varieties.

BRIEF SUMMARY OF SELECTED EMBODIMENTS OF THE PRESENT INVENTION

Embodiments of the present invention relate generally to new forage crops and methods of creating new forage crops.

In a specific embodiment, the present invention relates to new varieties of *sorghum* that do not produce dhurrin. In a still further embodiment, the present invention relates to new varieties of *sorghum* that do not produce dhurrin but have a standard growth rate. In an example, the *sorghum* genome is mutated via chemical mutagenesis and mutants are identified that produce no dhurrin. In some embodiments, the mutant plants comprise the genetic mutation present in the plant mutants identified as Tx623(EMS)2447 and Tx623(EMS)5085 and hence the mutant plants do not produce dhurrin.

In one embodiment, a method of producing a *sorghum* plant with altered dhurrin content or catabolism as compared to a control *sorghum* plant is provided. The method comprises inducing mutagenesis by applying a chemical mutagen to a reproductive portion of a *sorghum* plant; producing a population of mutant *sorghum* plants using the treated reproductive portion; assaying the population of mutant *sorghum* for altered dhurrin content; and growing the mutant *sorghum* plant, wherein the mutant *sorghum* plant exhibits altered dhurrin content or catabolism as compared to a control *sorghum* plant.

In some embodiments, the mutant *sorghum* plant has the same genetic mutation or mutations that result in lack of dhurrin production in the mutant plants identified as Tx623(EMS)2447 and Tx623(EMS)5085.

In some embodiments, the mutant *sorghum* plant exhibits decreased dhurrin content as compared to the control *sorghum* plant. In some embodiments, the mutant *sorghum* plant is substantially dhurrin-free as compared to a control *sorghum*. In some embodiments, the mutant *sorghum* plant exhibits no significant difference in growth rate as compared to the control *sorghum* plant. For example, the photosynthetic properties, maturation rate, and/or the biomass accumulation are not significantly different between the mutant *sorghum* plant as compared to the control *sorghum* plant. In an embodiment, there is no significant difference in chlorophyll concentration between mutant plants identified as Tx623(EMS)2447 and Tx623(EMS)5085 as compared to control *sorghum* plants. In a further embodiment, the mutant *sorghum* plants produce dhurrin but lack the ability to catabolize dhurrin to HCN.

The features, functions, and advantages that have been discussed may be achieved independently in various embodiments of the present invention or may be combined with yet other embodiments, further details of which can be seen with reference to the following description and drawings.

BRIEF DESCRIPTION OF THE SEVERAL VIEWS OF THE DRAWINGS

Figure 1:
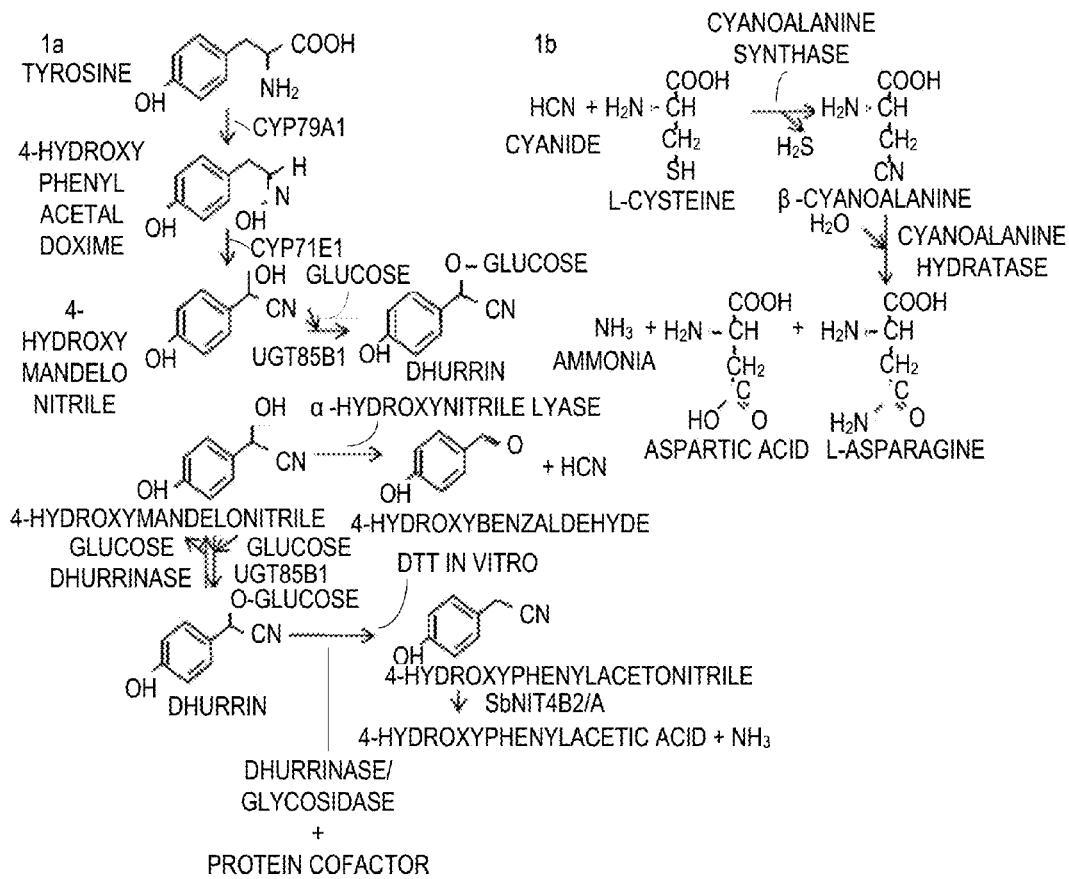
Figure 2:
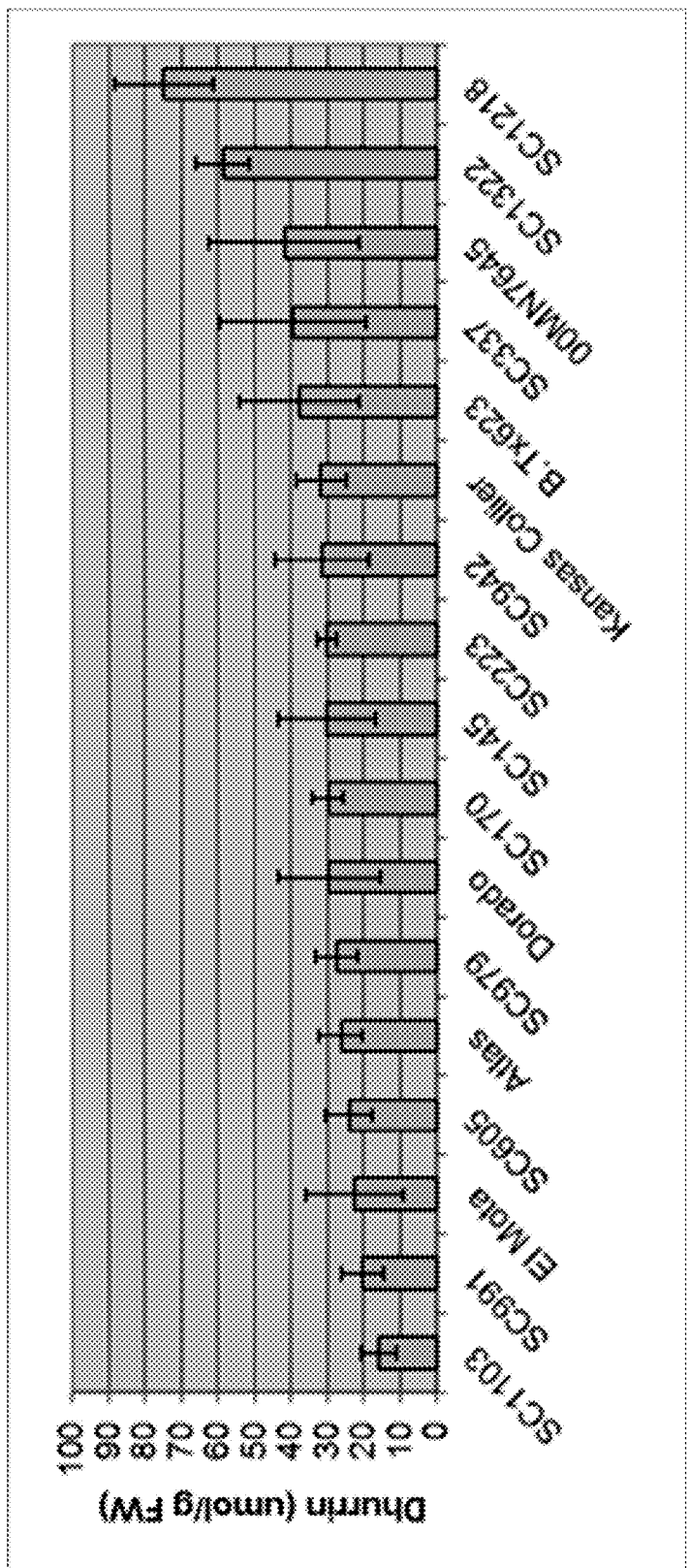
Figure 3:
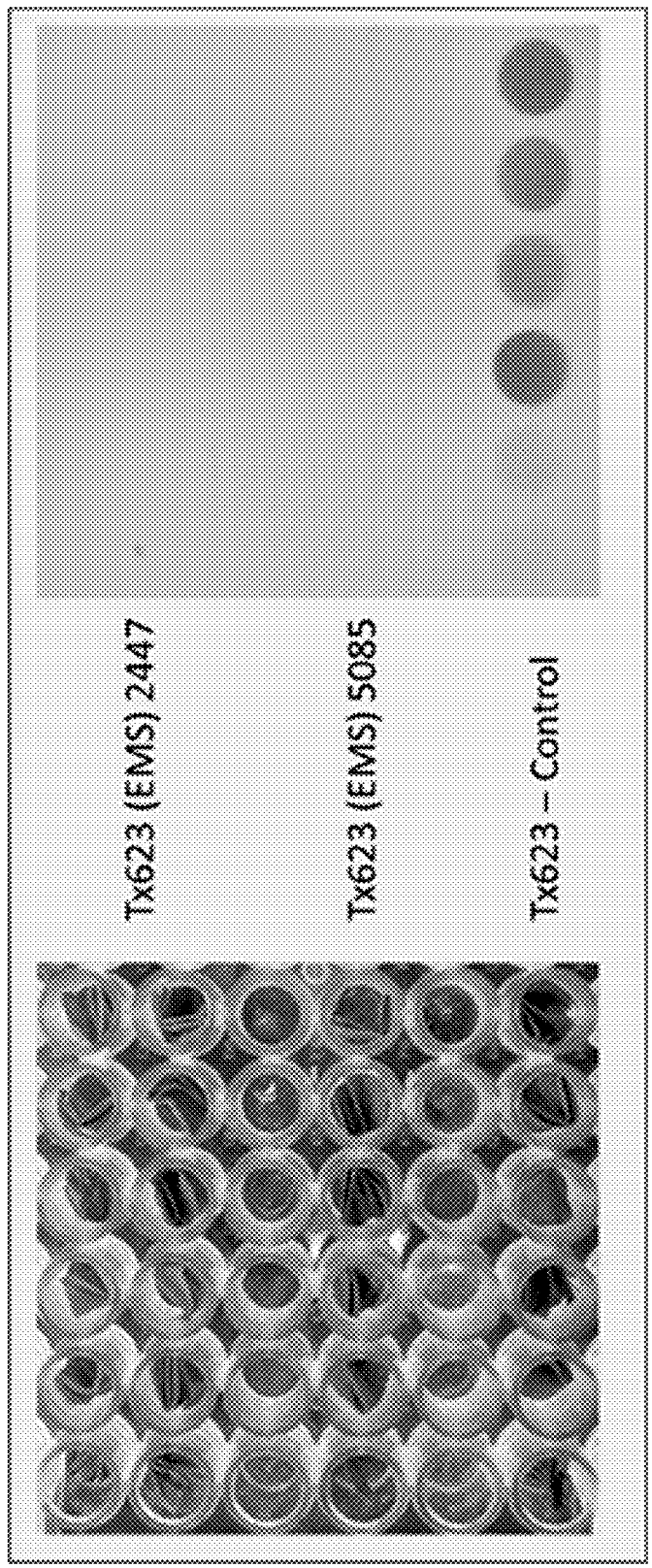
Figure 4:
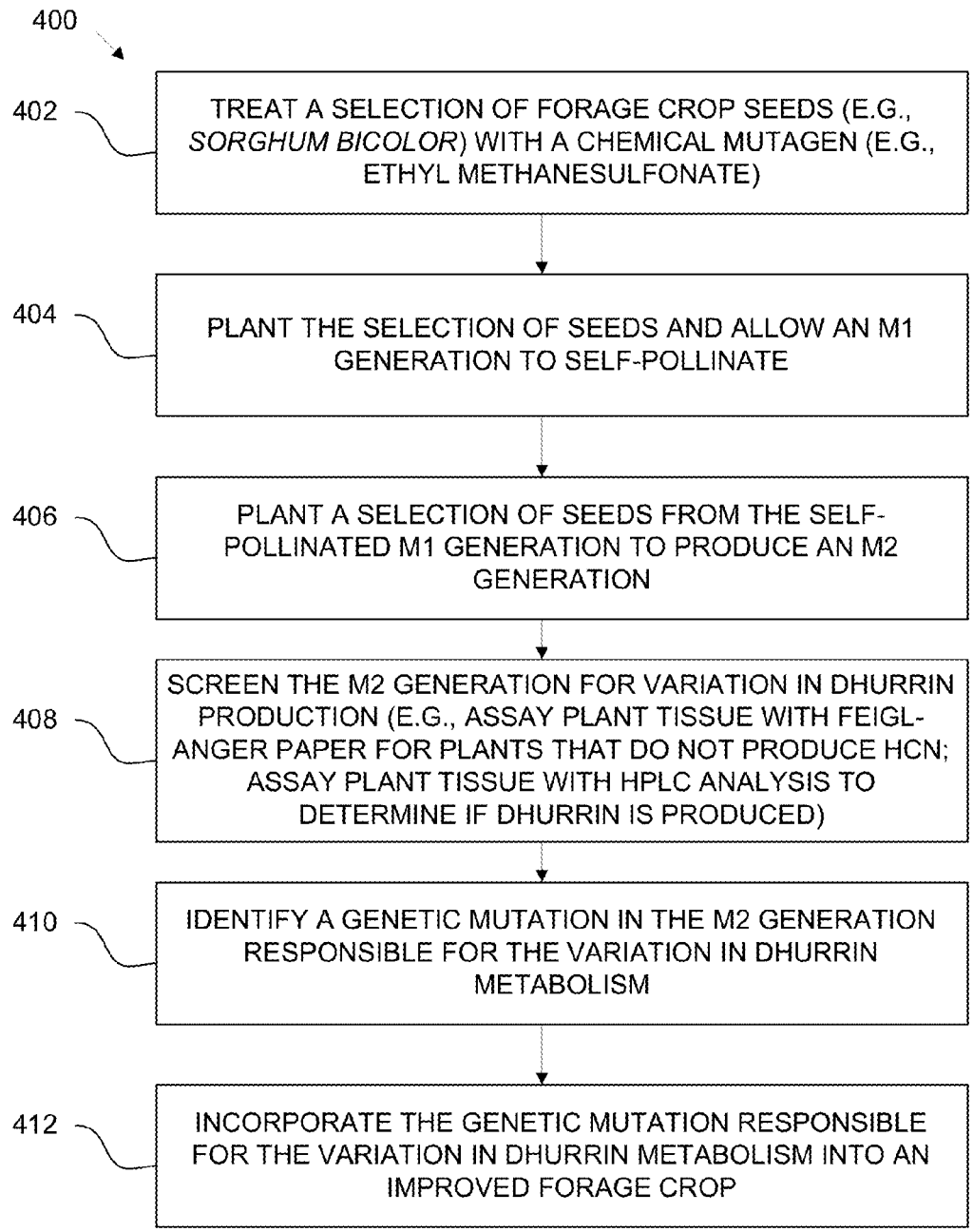

Having thus described embodiments of the present invention in general terms, reference will now be made to the accompanying drawings, which are not necessarily drawn to scale, and wherein:

FIG. 1*a* shows a model of the dhurrin biosynthesis, catabolism, and turnover in plants;

FIG. 1*b* shows a model of an HCN detoxification pathway in higher plants;

FIG. 2 shows a screen for dhurrin content in a selection of genotypes representing the phenotypic extremes of predicted dhurrin content;

FIG. 3 shows the results of the Feigl-Anger paper assay indicating release of HCN from leaf tissue in control plants but not in Tx623(EMS)2447 or Tx623(EMS)5085;

FIG. 4 depicts a flow chart of a method for producing dhurrin-free forage crops in accordance with one embodiment of the invention; and FIG. 5 depicts the wild-type and mutant amino acid sequence of CYP79A1 from the Tx623(EMS)2447 and Tx623(EMS)5085 dhurrin mutants.

DETAILED DESCRIPTION OF EMBODIMENTS OF THE PRESENT INVENTION

Embodiments of the present invention now will be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure will satisfy applicable legal requirements. Additionally, while embodiments are disclosed as "comprising" elements, it should be understood that the embodiments may also "consist of" elements or "consist essentially of" elements. Where possible, any terms expressed in the singular form herein are meant to also include the plural form and vice versa unless explicitly stated otherwise. Also, as used herein, the term "a" and/or "an" shall mean "one or more," even though the phrase "one or more" is also used herein. Like numbers refer to like elements throughout.

Embodiments of the present invention relate generally to new forage crops and methods of creating new crops. Chemical mutagenesis and screening for variation in plants is a promising technique for creating new forage crops with desired traits. Examples of desirable traits for forage crops include, but are not limited to, crops that do not produce cyanogenic glucosides such as dhurrin, crops that do not produce hydrogen cyanides, and crops that have a standard growth rate compared to existing commercial varieties.

In some embodiments, the crops of the present invention are annual grasses, such as members of the Poaceae plant family. The species may also be biennials or perennials depending on cultivar and species. In an exemplary embodiment, the crop is a member of the genus *Sorghum*, such as the cultivated species *S. bicolor*. *S. bicolor* can grow in arid solids and withstand prolonged droughts. It has a large root-to-leaf surface area and will roll its leaves in times of drought to lessen water loss by transpiration. *S. bicolor* is a C4 plant and hence it has improved photosynthetic efficiency and reduced water loss in hot or dry environments. Development of *sorghum* with altered dhurrin content or catabolism is therefore desirable as it improves a highly drought tolerant forage crop. Dhurrin-free forage crops are less likely to sicken domesticated animals when used as a feed.

In FIG. 2, a set of three hundred genotypes from a panel of *sorghum* conversion lines and advanced breeding lines (Casa et al., 2008) was screened to determine the extent of natural genetic variation for dhurrin content in *sorghum*. The initial survey utilized a spectrometric approach to estimate differences in dhurrin content among lines (Gorz et al., 1977). Genotypes representing the phenotypic extremes of predicted dhurrin content were re-analyzed by HPLC. These experiments demonstrated a 5-fold variation among lines with a few entries showing extremely high- or low-dhurrin content. None of the genotypes represented a dhurrin-free phenotype.

Researchers have attempted to improve *sorghum* as a forage crop through breeding programs. Unfortunately, the lack of genetic variation in dhurrin production has made it difficult to breed crop varieties that do not produce dhurrin.

Chemical mutagenesis is a process by which the genes of an organism are changed by exposure to chemical mutagens. In an embodiment, ethyl methanesulfonate can be used as a chemical mutagen to produce a population of *sorghum* mutants having a greater range of variation in dhurrin content than available in the natural gene pool. Ethyl methanesulfonate is a mutagenic organic compound with the formula $CH_3SO_3C_2H_5$. Ethyl methanesulfonate produces random mutations in genetic material by nucleotide substitution. In an embodiment, ethyl methanesulfonate may be applied to seeds to induce genetic mutations in the seed genomes.

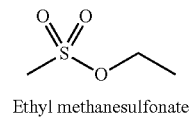

Ethyl methanesulfonate

In some embodiments, chemical mutagenesis is used to produce crops with altered cyanogenic glucoside composition. In an exemplary embodiment, ethyl methanesulfonate (EMS) mutagenesis is used to produce *sorghum* with lowered dhurrin content. Annual grasses such as sorghums (*Sorghum* spp.) are appealing candidates for creating new forage crops. As used herein, the term "*sorghum*" refers to all of the *Sorghum* spp., including hybrids.

In one embodiment, a method of producing a *sorghum* plant with altered dhurrin content or catabolism as compared to a control *sorghum* plant is provided. The method comprises inducing mutagenesis by applying a chemical mutagen to a reproductive portion of a *sorghum* plant; producing a population of mutant *sorghum* plants using the treated reproductive portion; assaying the population of mutant *sorghum* for altered dhurrin content; and growing the mutant *sorghum* plant, wherein the mutant *sorghum* plant exhibits altered dhurrin content or catabolism as compared to a control *sorghum* plant.

In some embodiments, the chemical mutagen is ethyl methanesulfonate. Alkaloids such as diethyl sulfate (DES) or dimethyl sulfate may be used instead of or in addition to ethyl methanesulfonate. Other chemical mutagens may also be used.

In some embodiments, the mutated *sorghum* plant exhibits altered dhurrin content or catabolism in the form of decreased dhurrin content as compared to the control *sorghum* plant. In some embodiments, the mutated *sorghum* plant exhibits altered dhurrin content or catabolism in the form of substantially no dhurrin content as compared to the control *sorghum* plant. In an embodiment, substantially no dhurrin content means dhurrin content undetectable by standard lab procedures. In some embodiments, the mutated *sorghum* plant exhibits altered dhurrin content or catabolism in the form of decreased or zero dhurrin content while retaining a standard growth rate. In one embodiment, the mutation of the *sorghum* plants results in at least one plant not producing dhurrin while still having a standard, as opposed to reduced, growth rate at all stages of plant development compared to existing commercial varieties. The control *sorghum* plant can be a wild-type plant, a commercial or hybrid variety, or any other *sorghum* plant suitable for the purpose of comparison. In a still further embodiment, the mutant *sorghum* plant produces dhurrin but lacks at least one enzyme in the catabolic stages to convert dhurrin to HCN.

*Sorghum* is an attractive option for a forage crop for a number of reasons, including the following: it generally requires about half the water to grow compared to corn and exhibits excellent adaptation to low-input production systems. Additionally, there are abundant genomic resources (sequence, microarrays, etc.) available for analyzing *sorghum*. Genotypes are adapted to growing across a wide geographical range and many pedigrees are available, allowing for cultivation of *sorghum* in a wide variety of environments.

As noted above, development of forage crops with altered dhurrin content or catabolism is desirable as it improves forage quality, possibly by reducing or removing the production of HCN. In many plant bioenergy crops, such as *sorghum*, barley (*Hordium vulgara* L.), and cassava (*Manihot esculenta* Crantz.), dhurrin is produced and causes HCN to be produced when the biomass is crushed, macerated, or otherwise disturbed. Further, dhurrin content increases during times of plant stress or nitrogen-enrichment. The availability of dhurrin-free forage biomass with low or no-dhurrin reduces threats to livestock.

Having discussed the importance of *sorghum* as a forage crop, the problem of dhurrin content in *sorghum*, and the limitations related to producing dhurrin-free varieties, an example is now provided disclosing the production of two dhurrin-free *sorghum* varieties. An exemplary flowchart of the method used to produce forage crops having altered dhurrin concentration is presented in FIG. 4. In this example, ethyl methanesulfonate (EMS) mutagenesis was used to produce a population of *sorghum* mutants having a greater range of variation in dhurrin content than available in the natural gene pool. Approximately 1.5 kg seeds of BTx623, the genotype of the sequenced genome, were treated with 45 mM EMS (402) and the seeds were planted under field conditions (404). The M1 panicles were allowed to self-pollinate then hand-harvested and threshed to produce approximately 12,000 M2 families.

Next, the M2 families were screened for variation in dhurrin metabolism by planting seeds in sand benches in a greenhouse (406) and evaluating 10-12 young seedlings per family at the 2- to 3-leaf stage. A portion of the upper-leaf was sampled into 96-well plates and frozen at −80° C. overnight. In the morning, the plates were covered with Feigl-Anger paper (Feigl and Anger, 1966) and thawed at 35° C. for 30 minutes. Blue spots on the Feigl-Anger paper indicated release of HCN from the leaf tissue (408). FIG. 3 depicts the results of the Feigl-Anger paper assay for mutants Tx623(EMS)2447 and Tx623(EMS)5085 as compared to the wild-type. This high-throughput assay provided a powerful screen for identification of plants compromised in dhurrin biosynthesis or catabolism.

In some embodiments, the nucleotide sequence for Tx623(EMS)2447 and Tx623(EMS)5085 or other mutants depicting impaired dhurrin concentration can be determined, the mutant sequence compared to the wild-type sequence, and the genetic mutation responsible for the decreased dhurrin concentration determined (410). In a still further embodiment of the method, this genetic mutation can be incorporated into forage crops in order to produce a mutated forage crop having altered dhurrin production (412).

A comparison of HCN release in numerous pairs of white and green siblings from M2 families segregating for albinism showed that even albino plants produce large-quantities of HCN. This indicated that photosynthesis was not required for dhurrin accumulation in young seedling tissues. The dhurrin produced in albino tissues must be synthesized from precursors stored and released from the endosperm reserves. Based on these results, mutants identified in a screen for HCN release may not only indicate lesions in dhurrin metabolism but also genes involved in precursor biosynthesis and transport.

A forward genetic screen of 5,000 M2 families identified several mutants impaired in HCN production. HPLC analysis was used to determine if these mutants were capable of producing dhurrin. Plants were grown in a greenhouse. The youngest fully expanded leaf from seedlings and adult plants was sampled and the fresh weight recorded. The leaf samples were then immersed in 50% methanol maintained at 75° C. for 15 minutes to inactivate the catabolic enzymes. The samples were ground and suspended in 500 µl of 50% methanol. A Shim-pack XR-ODS column (3.0×75 mm, 2.2 mm) (Shimadzu, Kyoto, Japan) was used to analyze the samples as previously described (De Nicola et al., 2011). The results from these studies indicated that many mutants that could not produce HCN were able to produce dhurrin. These mutants represent lesions in genes associated with dhurrin catabolism.

However, as shown in FIG. 3, mutant plants from Tx623 (EMS)2447 and Tx623(EMS)5085 did not produce dhurrin (Table 1). Note also that the wild type genotope, when used as a comparison, produced 24.1 µmol/g FW.

TABLE 1

HPLC analysis of the chemical composition of *sorghum* mutants displaying disruption in dhurrin biosynthesis.

| Mutant Family | Genotype[1] | Dhurrin (µmol/g[-1] FW)[2] |
|---|---|---|
| Tx623(EMS)2447 | WT | 24.1 |
|  | HCN– | 0 |
| Tx623(EMS)5085 | WT | 30.4 |
|  | HCN– | 0 |
| BTx623 | WT - check | 28.0 |

[1]WT = wild-type segregate; HCN– = mutant segregate
[2]FW = leaf fresh-weight

The mutant plants grew normally and showed no differences in relative greenness at 53 days after planting (Table 2).

TABLE 2

Variation in relative leaf greenness of wild type and dhurrin mutant seedling plants at 53 days after planting measured using a CCM-200. Plants were grown in field trials in West Lafayette, IN 2012.

| Mutant Family | Genotype[1] | Relative Greenness[2] |
|---|---|---|
| Tx623(EMS)2447 | HCN– | 48.3 |
| Tx623(EMS)5085 | HCN– | 48.9 |
| BTx623 | WT - check | 44.8 |
| Significance |  | NS |

[1]WT = wild-type segregate; HCN– = mutant segregate
[2]NS = No significant difference among genotypes Analyses of plant growth at 91 days after planting showed no significant differences in plant dry weight (Table 3).

TABLE 3

Variation in plant dry weight of wild type and dhurrin mutant seedling plants selected from mutant families Tx623(EMS)2447 and Tx623(EMS)5085 at 91 days after planting. Plants were grown in field trials in West Lafayette, IN 2012.

| Mutant Family | Genotype[1] | Dry Weight[2] (g plant[-1]) |
|---|---|---|
| Tx623(EMS)2447 | HCN+ | 136 |
| Tx623(EMS)2447 | HCN– | 143 |
| Tx623(EMS)5085 | HCN+ | 170 |
| Tx623(EMS)5085 | HCN– | 129 |
| Significance |  | NS |

[1]WT = wild-type segregate; HCN– = mutant segregate
[2]NS = No significant difference among genotypes Analysis of genetic inheritance of these mutations showed that the mutations were recessive (Table 4). Analysis of segregating families derived from Tx623(EMS)2447 indicated segregation ratios consistent with the effects of a single major recessive gene.

TABLE 4

Genetic inheritance of mutations that disrupt dhurrin biosynthesis.

| Mutant Family | Inheritance | Genetic Segregation[1] WT | Genetic Segregation[1] HCN– | Expected Segregation | Significance |
|---|---|---|---|---|---|
| Tx623(EMS)2447 | Recessive | 34 | 14 | 3:1 | Not Significant |
| Tx623(EMS)5085 | Recessive | NA | NA | NA | NA |

[1]WT = wild-type segregate; HCN– = mutant segregate; NA = Not available

Whole genome sequencing of Tx623(EMS)2447 and Tx623(EMS)5085 genotypes showed that both mutants harbored a C493Y mutation in the CYP79A1 gene that disrupts dhurrin biosynthesis. The wild type (SEQ ID NO: 1) and mutant (SEQ ID NO: 2) amino acid sequences are disclosed in FIG. 5. The cysteine to tyrosine mutation at position 493 in CYP97A1 disrupts dhurrin biosynthesis.

In another embodiment, the present invention comprises a method of producing a *sorghum* plant having the genetic mutation or mutations present in Tx623(EMS)2447 and/or Tx623(EMS)5085 such that the *sorghum* plant does not accumulate dhurrin or release HCN. In an embodiment, the method comprises inducing mutagenesis by applying a ethyl methanesulfonate to a seed of a *sorghum* plant; producing a population of mutant *sorghum* plants using the treated seeds; assaying the population of mutant *sorghum* for mutant *sorghum* plants having the mutation present in Tx623(EMS) 2447 or Tx623(EMS)5085; and growing the mutant *sorghum* plant, wherein the mutant *sorghum* plant exhibits substantially zero dhurrin content as compared to a control *sorghum* plant. In some embodiments, the genetic mutation is a genetic mutation that is highly homologous to the genetic mutation in Tx623(EMS)2447 or Tx623(EMS)5058. The homology may be as high as, for example, 60, 65, 70, 75, 80, 85, 80, 95, or 100% at the nucleotide sequence level. Other methods of introducing the C493Y mutation in CYP79A1 into plants or plant cells are possible. For example, a recombinagenic oligonucleotide can be introduced into a plant cell using any method commonly used in the art, including but not limited to, microcarriers (biolistic delivery), microfibers, electroporation, and microinjection.

In some embodiments, the Tx623(EMS)2447 or Tx623 (EMS)5085 *sorghum* plant exhibits altered dhurrin content or catabolism in the form of decreased dhurrin content as compared to the control *sorghum* plant. In some embodiments, the Tx623(EMS)2447 or Tx623(EMS)5085 *sorghum* plant exhibits altered dhurrin content or catabolism in the form of zero dhurrin content as compared to the control *sorghum* plant. In some embodiments, the Tx623(EMS) 2447 or Tx623(EMS)5085 *sorghum* plant exhibits altered dhurrin content or catabolism in the form of decreased (e.g., zero) dhurrin content but retaining a standard growth rate as compared to the control *sorghum* plant. The control *sorghum* plant can be a wild-type plant, a commercial or hybrid crop variety, or any other *sorghum* plant suitable for the purpose of comparison.

The Tx623(EMS)2447 and Tx623(EMS)5085 mutants described in this disclosure were shown to be dhurrin-free. Whole genome sequencing of the Tx623(EMS)2447 and Tx623(EMS)5085 genotypes showed that both mutants harbored a C493Y mutation in the CYP79A1 gene that disrupts dhurrin biosynthesis (FIG. 5). These mutants do not produce measurable dhurrin and do not exhibit a slow-growth phenotype.

Although this description mainly refers to using embodiments of the invention in conjunction with the Tx623(EMS) 2447 and Tx623(EMS)5085 genotypes, it should be appreciated that these embodiments may be used to induce other mutations in *sorghum* for modulating or altering dhurrin content or catabolism.

Given the normal growth pattern of these dhurrin-free mutants, the dhurrin-free mutants identified in this disclosure may provide an alternative genetic resource for modifying dhurrin production in *sorghum*. On a national and global scale, development of dhurrin-free *sorghum* grain, forage, and biomass cultivars has the potential to replace corn and other forage crops that have lower water-use efficiency characteristics resulting in reduced water requirements for irrigation.

Specific embodiments of the invention are described herein. Many modifications and other embodiments of the invention set forth herein will come to mind to one skilled in the art to which the invention pertains having the benefit of the teachings presented in the foregoing descriptions and the associated drawings. Therefore, it is to be understood that the invention is not to be limited to the specific embodiments disclosed and that modifications and other embodiments and combinations of embodiments are intended to be included within the scope of the appended claims. Although specific terms are employed herein, they are used in a generic and descriptive sense only and not for purposes of limitation.

REFERENCES

Akazawa, T., P. Miljanich, et al. (1960). "Studies on the cyanogenic glucoside of *Sorghum vulgare*." Plant Physiol 35: 535-538.
Anon (1897). "Effects of *sorghum*." New South Wales Agricultural Gazette 8: 275-276.
Bak, S., S. Paquette, et al. (2006). "Cyanogenic glucosides: a case study for evolution and application of cytochromes P450." Phytochem Rev 5: 309-329.
Banea-Mayambu, J. P., T. Tylleskar, et al. (1997). "Geographical and seasonal association between linamarin and cyanide exposure from cassava and the upper motor neurone disease Konzo in former Zaire" Trop. Med. Int. Health 2: 1143-1151.
Banea-Mayambu, J. P., T. Tylleskar, et al. (2000). "Dietary cyanide from insufficiently processed cassava and growth retardation in children in the Democratic Republic of Congo (formerly Zaire)." Ann. Trop. Paediatr 20: 34-40.
Blomstedt, C. K., et al. (2012). "A combined biochemical screen and TILLING approach identifies mutations in *Sorghum bicolor* L. Moench resulting in acyanogenic forage production." Plant Biotechnology Journal 10: 54-66.
Boyd, F. T., O. S. Aamodt, et al. (1938). "Sudan grass management for control of cyanide poisoning." J Am Soc Agron 30: 569-582.
Brattsten, L. B., J. H. Samuelian, et al. (1983). "Cyanide as a feeding stimulant for the southern armyworm, Spodoptera eridania." Ecol. Entomology 8: 125-132.
Casa, A. M. (2008). "Community resources and strategies for association mapping in *sorghum*." Crop Science 48: 30-40.
Conn, E. E. (1981). Cyanogenic glycosides. The biochemistry of plants. New York, Academic. 7: 479-500.
Conn, E. E. (1994). "Cyanogenesis—a personal perspective." Acta Hort. 375: 31-43.
Davis, R. H. and A. Nahrstedt (1985). Cyanogenesis in insects. Comprehensive Insect Physiology, Biochemistry and Pharmacology. G. A. Kerkut and L. I. Gilbert. Oxford, Pergamon Press: 635-654.
De Nicola, G. R., Leoni, O., Malaguti, L., Bernardi, R., Lazzeri, L. (2011) A simple analytical method for dhurrin content evaluation in cyanogenic plants for their utilization in fodder and, biofumigation J. Agric. Food Chem., 59: 8065-8069
Feigl, F. and V. Anger (1966). "Replacement of benzidine by copper ethylacetoacetate and tetra base as spot-test reagent for hydrogen cyanide and cyanogen." Analyst (Lond.) 91: 282-284.
Goodstein, D. M. et al., Phytozome: a comparative platform for green plant genomics, Nucleic Acids Res. 2012 40 (Dl): D1178-D1186
Gorz, H. J., W. L. Haag, et al. (1977). "Assay of p-hydroxybenzaldehyde as a measure of hydrocyanic acid potential in sorghums." Crop Science 17: 578-582.
Halkier, B. A. and B. L. Moller (1989). "Biosynthesis of the cyanogenic glucoside dhurrin in seedlings of *Sorghum-bicolor* (L.) Moench and partial-purification of the enzyme-system involved." Plant Physiol 90: 1552-1559.
Hopkins, A. (1995). Factors influencing cattle bracken-poisoning in Great Britain. Bracken: An Environmental Issue. T. Smith and J. A. Taylor. Aberystwyth, Wales, International Bracken Group Special Publication. 2: 120-123.
Jaroszewski, J. W., E. S. Olafsdottir, et al. (2002). "Cyanohydrin glycosides of Passiflora: distribution pattern, a saturated cyclopentane derivative from P. guatemalensis, and formation of pseudocyanogenic [alpha]-hydroxyamides as isolation artefacts." Phytochemistry 59(5): 501-511.
Jones, P. R., M. D. Andersen, et al. (2000). The biosynthesis, degradation, transport and possible function of cyanogenic glucosides. Evolution of Metabolic Pathways. J. T. Romero, R. Ibrahim, L. Varin and V. De Luca. New York, Elsevier Science: 191-247.
Lin, Y. R., K. F. Schertz, et al. (1995). "Comparative analysis of QTLs affecting plant height and maturity across the Poaceae, in reference to an interspecific *sorghum* population." Genetics 141: 391-411.
Oluwole, O. S. A., A. O. Onabolu, et al. (2000). "Persistence of tropical ataxic neuropathy in a Nigerian community." J Neurol Neurosurg Psychiatr 69: 96-101.

Osbourn, A. E. (1996). "Preformed antimicrobial compounds and plant defense against fungal attack." Plant Cell 8: 1821-1831.

Paterson A. H., et al. (2009). "The *Sorghum bicolor* genome and the diversification of grasses." Nature 457,551-556.

Prasad, S., et al. 2011. "Determination and detoxification of cyanide content in *sorghum* for ethanol production using *Saccharomyces cerevisiae* strain." Journal of Metabolomics and Systems Biology. 2: 10-14.

Robinson, M. E. (1930). "Cyanogenesis in plants." Biol. Rev. 5: 126-142.

Siegler, D. S. and A. M. Brinker (1993). Characterisation of cyanogenic glycosides, cyanolipids, nitroglycosides, organic nitro compounds and nitrile glycosides from plants. Methods of plant biochemistry, alkaloids and sulfur compounds. P. M. Dey and J. B. Harborne. New York, Academic: 51-93.

Stephens, J. C., F. R. Miller, et al. (1967). "Conversion of alien sorghums to early combine genotypes." Crop Science 7: 396.

Vanetten, H. D., J. W. Mansfield, et al. (1994). "2 classes of plant antibiotics—phytoalexins versus phytoanticipins." Plant Cell 6: 1191-1192.

Varshney, J. P., A. K. Gupta, et al. (1996). "Occurrence of ataxia-cystitis syndrome in horses fed on *Sorghum vulgare* in India." Indian Veterinary Journal 73: 985-986.

Vetter, J. (2000). "Plant cyanogenic glycosides." Toxicon 38: 11-36.

Webber, J. J., C. R. Roycroft, et al. (1985). "Cyanide poisoning of goats from sugar gums (Eucalyptus cladocalyx)." Aust. Vet. J.: 62:28.

Zagrobelny, M., S. Bak, et al. (2008). "Cyanogenesis in plants and arthropods." Phytochemistry 69: 1457-1468.

What is claimed is:

1. A mutant *sorghum* plant comprising a mutation in a CYP79A1 gene, wherein the mutation disrupts dhurrin biosynthesis, wherein the mutation is a C493Y mutation in the CYP79A1 gene.

2. The mutant *sorghum* plant of claim 1, wherein the mutant *sorghum* plant comprises a gene encoding an amino acid sequence comprising SEQ ID NO: 2.

3. The mutant *sorghum* plant of claim 1, wherein the disrupted dhurrin biosynthesis results in a reduced dhurrin concentration or catabolism.

4. The mutant *sorghum* plant of claim 3, wherein the reduced dhurrin concentration is a substantially zero dhurrin concentration.

5. The mutant *sorghum* plant of claim 1, wherein the altered dhurrin catabolism is an inability to catabolize dhurrin to HCN.

6. The mutant *sorghum* plant of claim 1, wherein the mutant *sorghum* exhibits no significant difference in growth rate compared to a control *sorghum*.

7. A method of producing a *sorghum* plant with altered dhurrin content or catabolism as compared to a control *sorghum* plant, the method comprising:
   inducing mutagenesis by applying a chemical mutagen to a reproductive portion of a *sorghum* plant;
   producing a population of mutant *sorghum* plants using the treated reproductive portion;
   assaying the population of mutant *sorghum* for altered dhurrin content, wherein the mutant *sorghum* plant identified in the assay comprises a C493Y mutation in a CYP79A1 gene; and
   growing the mutant *sorghum* plant identified in the assay, wherein the mutant *sorghum* plant exhibits altered dhurrin content or catabolism as compared to a control *sorghum* plant.

8. The method of claim 7, wherein the mutant *sorghum* plant comprises a gene encoding an amino acid sequence comprising SEQ ID NO: 2.

9. The method of claim 7, wherein the mutant *sorghum* plant exhibits decreased dhurrin content as compared to the control *sorghum* plant.

10. The method of claim 7, wherein the mutant *sorghum* plant exhibits substantially zero dhurrin content.

11. The method of claim 7, wherein the mutant *sorghum* plant exhibits an inability to catabolize dhurrin as compared to the control *sorghum* plant.

12. The method of claim 7, wherein the chemical mutagen is ethyl methanesulfonate.

13. The method of claim 7, wherein the reproductive portion is selected from the group consisting of a seed, a rhizome, a cutting, and a tissue cloning sample.

14. The method of claim 7, wherein the mutant *sorghum* plant exhibits no significant difference in growth rate as compared to the control *sorghum* plant.

15. A method of producing a *sorghum* plant cell with altered dhurrin content or catabolism as compared to a control *sorghum* plant, the method comprising:
   introducing into a plant cell a recombinagenic oligonucleotide with a targeted mutation in a CYP79A1 gene to produce plant cells having a C493Y mutation; and
   identifying the plant cell having a C493Y mutation in the CYP79A1 gene, wherein the plant cell exhibits altered dhurrin content or catabolism as compared to a control *sorghum* plant.

16. The method of claim 15, wherein the *sorghum* plant cell exhibits no significant difference in growth rate as compared to the control *sorghum* plant.

17. The method according to claim 15, wherein the recombinagenic oligonucleotide is introduced by electroporation, biolistic transformation or polyethylene glycol precipitation.

18. The method of claim 15, wherein the plant cell expresses an amino acid sequence comprising SEQ ID NO: 2.

* * * * *

SEQUENCE LISTING

```
<160> NUMBER OF SEQ ID NOS: 2

<210> SEQ ID NO 1
<211> LENGTH: 558
<212> TYPE: PRT
<213> ORGANISM: Sorghum bicolor

<400> SEQUENCE: 1

Met Ala Thr Met Glu Val Glu Ala Ala Ala Thr Val Leu Ala Ala
1               5                   10                  15

Pro Leu Leu Ser Ser Ser Ala Ile Leu Lys Leu Leu Leu Phe Val Val
                20                  25                  30

Thr Leu Ser Tyr Leu Ala Arg Ala Leu Arg Arg Pro Arg Lys Ser Thr
                35                  40                  45

Thr Lys Cys Ser Ser Thr Thr Cys Ala Ser Pro Pro Ala Gly Val Gly
        50                  55                  60

Asn Pro Pro Leu Pro Pro Gly Pro Val Pro Trp Pro Val Val Gly Asn
65                  70                  75                  80

Leu Pro Glu Met Leu Leu Asn Lys Pro Ala Phe Arg Trp Ile His Gln
                85                  90                  95

Met Met Arg Glu Met Gly Thr Asp Ile Ala Cys Val Lys Leu Gly Gly
                100                 105                 110

Val His Val Val Ser Ile Thr Cys Pro Glu Ile Ala Arg Glu Val Leu
        115                 120                 125

Arg Lys Gln Asp Ala Asn Phe Ile Ser Arg Pro Leu Thr Phe Ala Ser
        130                 135                 140

Glu Thr Phe Ser Gly Gly Tyr Arg Asn Ala Val Leu Ser Pro Tyr Gly
145                 150                 155                 160

Asp Gln Trp Lys Lys Met Arg Arg Val Leu Thr Ser Glu Ile Ile Cys
                165                 170                 175

Pro Ser Arg His Ala Trp Leu His Asp Lys Arg Thr Asp Glu Ala Asp
                180                 185                 190

Asn Leu Thr Arg Tyr Val Tyr Asn Leu Ala Thr Lys Ala Ala Thr Gly
        195                 200                 205

Asp Val Ala Val Asp Val Arg His Val Ala Arg His Tyr Cys Gly Asn
        210                 215                 220

Val Ile Arg Arg Leu Met Phe Asn Arg Arg Tyr Phe Gly Glu Pro Gln
225                 230                 235                 240

Ala Asp Gly Gly Pro Gly Pro Met Glu Val Leu His Met Asp Ala Val
                245                 250                 255
```

```
Phe Thr Ser Leu Gly Leu Leu Tyr Ala Phe Cys Val Ser Asp Tyr Leu
            260                 265                 270

Pro Trp Leu Arg Gly Leu Asp Leu Asp Gly His Glu Lys Ile Val Lys
        275                 280                 285

Glu Ala Asn Val Ala Val Asn Arg Leu His Asp Thr Val Ile Asp Asp
    290                 295                 300

Arg Trp Arg Gln Trp Lys Ser Gly Glu Arg Gln Glu Met Glu Asp Phe
305                 310                 315                 320

Leu Asp Val Leu Ile Thr Leu Lys Asp Ala Gln Gly Asn Pro Leu Leu
                325                 330                 335

Thr Ile Glu Glu Val Lys Ala Gln Ser Gln Asp Ile Thr Phe Ala Ala
            340                 345                 350

Val Asp Asn Pro Ser Asn Ala Val Glu Trp Ala Leu Ala Glu Met Val
        355                 360                 365

Asn Asn Pro Glu Val Met Ala Lys Ala Met Glu Glu Leu Asp Arg Val
    370                 375                 380

Val Gly Arg Glu Arg Leu Val Gln Glu Ser Asp Ile Pro Lys Leu Asn
385                 390                 395                 400

Tyr Val Lys Ala Cys Ile Arg Glu Ala Phe Arg Leu His Pro Val Ala
                405                 410                 415

Pro Phe Asn Val Pro His Val Ala Leu Ala Asp Thr Thr Ile Ala Gly
            420                 425                 430

Tyr Arg Val Pro Lys Gly Ser His Val Ile Leu Ser Arg Thr Gly Leu
        435                 440                 445

Gly Arg Asn Pro Arg Val Trp Asp Glu Pro Leu Arg Phe Tyr Pro Asp
    450                 455                 460

Arg His Leu Ala Thr Ala Ala Ser Asp Val Ala Leu Thr Glu Asn Asp
465                 470                 475                 480

Leu Arg Phe Ile Ser Phe Ser Thr Gly Arg Arg Gly Cys Ile Ala Ala
                485                 490                 495

Ser Leu Gly Thr Ala Met Ser Val Met Leu Phe Gly Arg Leu Leu Gln
            500                 505                 510

Gly Phe Thr Trp Ser Lys Pro Ala Gly Val Glu Ala Val Asp Leu Ser
        515                 520                 525

Glu Ser Lys Ser Asp Thr Phe Met Ala Thr Pro Leu Val Leu His Ala
    530                 535                 540

Glu Pro Arg Leu Pro Ala His Leu Tyr Pro Ser Ile Ser Ile
545                 550                 555

<210> SEQ ID NO 2
<211> LENGTH: 558
<212> TYPE: PRT
<213> ORGANISM: Artificial Sequence
<220> FEATURE:
<223> OTHER INFORMATION: Synthetic Construct

<400> SEQUENCE: 2

Met Ala Thr Met Glu Val Glu Ala Ala Ala Thr Val Leu Ala Ala
1               5                   10                  15

Pro Leu Leu Ser Ser Ser Ala Ile Leu Lys Leu Leu Phe Val Val
            20                  25                  30

Thr Leu Ser Tyr Leu Ala Arg Ala Leu Arg Arg Pro Arg Lys Ser Thr
        35                  40                  45

Thr Lys Cys Ser Ser Thr Thr Cys Ala Ser Pro Pro Ala Gly Val Gly
    50                  55                  60
```

```
Asn Pro Pro Leu Pro Pro Gly Pro Val Pro Trp Pro Val Val Gly Asn
 65                  70                  75                  80

Leu Pro Glu Met Leu Leu Asn Lys Pro Ala Phe Arg Trp Ile His Gln
             85                  90                  95

Met Met Arg Glu Met Gly Thr Asp Ile Ala Cys Val Lys Leu Gly Gly
            100                 105                 110

Val His Val Ser Ile Thr Cys Pro Glu Ile Ala Arg Glu Val Leu
        115                 120                 125

Arg Lys Gln Asp Ala Asn Phe Ile Ser Arg Pro Leu Thr Phe Ala Ser
        130                 135                 140

Glu Thr Phe Ser Gly Gly Tyr Arg Asn Ala Val Leu Ser Pro Tyr Gly
145                 150                 155                 160

Asp Gln Trp Lys Lys Met Arg Arg Val Leu Thr Ser Glu Ile Ile Cys
                165                 170                 175

Pro Ser Arg His Ala Trp Leu His Asp Lys Arg Thr Asp Glu Ala Asp
            180                 185                 190

Asn Leu Thr Arg Tyr Val Tyr Asn Leu Ala Thr Lys Ala Ala Thr Gly
            195                 200                 205

Asp Val Ala Val Asp Val Arg His Val Ala Arg His Tyr Cys Gly Asn
        210                 215                 220

Val Ile Arg Arg Leu Met Phe Asn Arg Arg Tyr Phe Gly Glu Pro Gln
225                 230                 235                 240

Ala Asp Gly Gly Pro Gly Pro Met Glu Val Leu His Met Asp Ala Val
                245                 250                 255

Phe Thr Ser Leu Gly Leu Leu Tyr Ala Phe Cys Val Ser Asp Tyr Leu
            260                 265                 270

Pro Trp Leu Arg Gly Leu Asp Leu Asp Gly His Glu Lys Ile Val Lys
            275                 280                 285

Glu Ala Asn Val Ala Val Asn Arg Leu His Asp Thr Val Ile Asp Asp
        290                 295                 300

Arg Trp Arg Gln Trp Lys Ser Gly Glu Arg Gln Glu Met Glu Asp Phe
305                 310                 315                 320

Leu Asp Val Leu Ile Thr Leu Lys Asp Ala Gln Gly Asn Pro Leu Leu
                325                 330                 335

Thr Ile Glu Glu Val Lys Ala Gln Ser Gln Asp Ile Thr Phe Ala Ala
            340                 345                 350

Val Asp Asn Pro Ser Asn Ala Val Glu Trp Ala Leu Ala Glu Met Val
        355                 360                 365

Asn Asn Pro Glu Val Met Ala Lys Ala Met Glu Glu Leu Asp Arg Val
            370                 375                 380

Val Gly Arg Glu Arg Leu Val Gln Glu Ser Asp Ile Pro Lys Leu Asn
385                 390                 395                 400

Tyr Val Lys Ala Cys Ile Arg Glu Ala Phe Arg Leu His Pro Val Ala
                405                 410                 415

Pro Phe Asn Val Pro His Val Ala Leu Ala Asp Thr Thr Ile Ala Gly
            420                 425                 430

Tyr Arg Val Pro Lys Gly Ser His Val Ile Leu Ser Arg Thr Gly Leu
            435                 440                 445

Gly Arg Asn Pro Arg Val Trp Asp Glu Pro Leu Arg Phe Tyr Pro Asp
        450                 455                 460

Arg His Leu Ala Thr Ala Ala Ser Asp Val Ala Leu Thr Glu Asn Asp
465                 470                 475                 480
```

-continued

```
Leu Arg Phe Ile Ser Phe Ser Thr Gly Arg Arg Gly Tyr Ile Ala Ala
                485                 490                 495

Ser Leu Gly Thr Ala Met Ser Val Met Leu Phe Gly Arg Leu Leu Gln
            500                 505                 510

Gly Phe Thr Trp Ser Lys Pro Ala Gly Val Glu Ala Val Asp Leu Ser
        515                 520                 525

Glu Ser Lys Ser Asp Thr Phe Met Ala Thr Pro Leu Val Leu His Ala
        530             535                 540

Glu Pro Arg Leu Pro Ala His Leu Tyr Pro Ser Ile Ser Ile
545                 550                 555
```